United States Patent
Afriat et al.

(10) Patent No.: US 6,905,695 B1
(45) Date of Patent: Jun. 14, 2005

(54) SOLID COMPOSITION AND ITS USES, IN PARTICULAR ITS COSMETIC USES

(75) Inventors: Isabelle Afriat, Paris (FR); Virginie Boulier, Paray Vieille-Poste (FR)

(73) Assignee: L'Oreal, Paris (FR)

( * ) Notice: Subject to any disclaimer, the term of this patent is extended or adjusted under 35 U.S.C. 154(b) by 183 days.

(21) Appl. No.: 09/610,320

(22) Filed: Jul. 5, 2000

(30) Foreign Application Priority Data

Jul. 12, 1999 (FR) ............................................ 99 09013

(51) Int. Cl.⁷ ................................................ A61K 7/00
(52) U.S. Cl. ........................ 424/401; 424/70.1; 424/59; 424/400
(58) Field of Search ................................ 424/400, 401, 424/59

(56) References Cited

U.S. PATENT DOCUMENTS

| | | | | |
|---|---|---|---|---|
| 5,250,289 A | * | 10/1993 | Boothroyd et al. | ............ 424/59 |
| 5,412,004 A | * | 5/1995 | Tachibana et al. | ............ 524/27 |
| 5,811,487 A | * | 9/1998 | Schulz, Jr. et al. | ......... 524/862 |
| 5,851,539 A | * | 12/1998 | Mellul et al. | ................ 424/401 |
| 5,919,468 A | * | 7/1999 | Bara | ........................... 424/401 |
| 5,935,559 A | | 8/1999 | Afriat et al. | |
| 6,168,782 B1 | * | 1/2001 | Lin et al. | ................. 424/78.03 |

FOREIGN PATENT DOCUMENTS

| | | | |
|---|---|---|---|
| EP | 0 612 517 | | 8/1994 |
| EP | 0 670 157 | | 9/1995 |
| EP | 0 965 331 | | 12/1999 |
| EP | 0 970 682 | | 1/2000 |
| KR | 9202286 B | * | 3/1992 |
| WO | WO 93/14742 | | 8/1993 |
| WO | WO 95/15812 | | 6/1995 |
| WO | WO 99/47111 | | 9/1999 |

* cited by examiner

*Primary Examiner*—Thurman K. Page
*Assistant Examiner*—Rachel M. Bennett
(74) *Attorney, Agent, or Firm*—Oblon, Spivak, McClelland, Maier & Neustadt, P.C.

(57) ABSTRACT

The invention relates to a solid composition in the form of a water-in-oil emulsion. The aqueous phase represents at least 70% by weight with respect to the total weight of the composition. The composition contains at least one silicone emulsifier and at least 3% by weight of at least one wax with respect to the total weight of the composition.

29 Claims, No Drawings

SOLID COMPOSITION AND ITS USES, IN PARTICULAR ITS COSMETIC USES

BACKGROUND OF THE INVENTION

1. Field of the Invention

The invention relates to a solid composition which is preferably provided in the form of a water-in-oil (W/O) emulsion and comprising a large amount of aqueous phase, at least one wax and a silicone emulsifier, and to the uses of the composition, in particular in the cosmetics and/or dermatological fields.

2. Discussion of the Background

In the cosmetics field, the freshness of products applied to the skin is a major preoccupation in hot countries or else in summer, where the need for refreshing textures is high.

Compositions giving an impression of freshness are conventionally obtained by using aqueous gels or oil-in-water emulsions, the external phase of which is aqueous. This is because, with aqueous gels or with emulsions comprising an external aqueous phase, the immediate effect felt during application to the skin is contributed by the water, which immediately evaporates, thus giving an impression of freshness.

Furthermore, the active principles present in an emulsion are more effective when they are in the dispersed phase of the emulsion. Thus, emulsions with an aqueous continuous phase (oil-in-water or O/W emulsions) allow the lipophilic active principles to be more effective, whereas emulsions with an oily continuous phase (water-in-oil or W/O emulsions) allow the hydrophilic active principles to be more effective. It is therefore advantageous also to have available W/O emulsions. However, W/O emulsions exhibit the disadvantage of being uncomfortable because of the greasy and heavy feeling contributed by the external fatty phase which remains on the skin. Thus, these emulsions do not contribute freshness and are generally too rich in oils to be used during the summer or in hot countries.

To overcome these disadvantages, the preparation of W/O emulsions with a high water content has been envisaged. However, the water content cannot be too high for reasons of stability, or else a high water content has to be compensated for by the addition of several surfactants or gelling agents which can be detrimental to the comfort of the final composition, and can even result in problems of cutaneous irritation, in particular for subjects with sensitive skin.

The need thus remains for a stable water-in-oil emulsions, which comprise a large amount of water and which can be used in the cosmetics and/or dermatological fields, which do not exhibit the disadvantages of the prior art.

SUMMARY OF THE INVENTION

The inventors have now discovered a solid composition of the water-in-oil emulsion type which makes it possible to achieve the above objectives and which in particular gives a strong impression of freshness although having an oily continuous phase.

One embodiment of the present invention is a solid composition comprising, an aqueous phase dispersed in an oily phase, where the aqueous phase represents at least 70% by weight with respect to the total weight of the composition, the composition comprises at least one silicone emulsifier and at least 3% by weight of at least one wax with respect to the total weight of the composition. The invention composition preferably is, or is a part of, a physiologically acceptable medium.

The term "physiologically acceptable medium" is understood to mean, in the context of the invention, a non-toxic medium capable of being applied to the skin (including the inside of the eyelids) or the lips of human beings.

Furthermore, the term "solid composition" is understood to mean a composition exhibiting a compressive strength of greater than or equal to 50 grams, at room temperature, after penetration by a cylindrical probe, generated by rotation, having a diameter of 0.8 cm into the matrix of the composition over a thickness of 5 mm at a rate of 1 mm/s, maintaining the said probe in the matrix of the composition for 15 seconds and withdrawing the probe from the matrix of the composition at a rate of 1 mm/s; the compressive strength being measured with a texture analyser of the TA.XT2 type sold by the company Rheo.

Despite the large amount of water, the composition of the invention is stable over time.

The composition according to the invention comprises at least 70% by weight of aqueous phase with respect to the total weight of the composition and preferably at least 75% of the total weight of the composition. The aqueous phase can constitute up to 92% of the total weight of the composition.

The water of the aqueous phase constitutes at least 65% and preferably 70% of the total weight of the composition.

Furthermore, the aqueous phase of the emulsion can comprise one or more lower alcohols, such as ethanol, in an amount preferably ranging up to 15% and better still up to 10% of the total weight of the composition and/or one or more polyols, such as glycerol and propylene glycol, in an amount ranging, for example, up to 20% and better still up to 10% of the total weight of the composition.

The composition of the invention comprises, as emulsifying agent, a silicon emulsifier. The latter generally has an HLB (Hydrophilic-Lipophilic Balance) of less than 8 and can be chosen in particular from dimethicone copolyols, alkyl or alkoxy dimethicone copolyols and crosslinked elastomeric solid organopolysiloxanes comprising at least one oxyalkylenated group, and their mixtures.

Dimethicone copolyols which can be used in the emulsion according to the invention include, for example, the following mixtures sold by the company Dow Corning:

mixture of dimethicone copolyol, of tetracyclomethicone (D4) and of water (ratio by weight 10/88/2), sold under the name DC 3225C;

mixture of dimethicone copolyol, of pentacyclomethicone (D5) and of water (ratio by weight 10/88/2), sold under the name DC 5225C;

mixture of dimethicone copolyol and of polydimethylsiloxane 5 cSt (ratio by weight 10/90), sold under the name DC 3225C in 200 Fluid 5 cSt;

mixture of dimethicone copolyol and of polydimethylsiloxane 10 cSt (ratio by weight 10/90), sold under the name DC 3225C in 200 Fluid 10 cSt;

mixture of dimethicone copolyol and of pentacyclomethicone (D5) (ratio by weight 43/57), sold under the name DC 5185C, and the product sold under the name "SF-1228" by the Company General Electric.

Useful alkyl dimethicone copolyols, include for example, lauryl dimethicone copolyol, such as that sold under the name Q2-5200 by the Company Dow Corning, cetyl dimethicone copolyol, such as that sold under the name Abil EM90 by the Company Goldschmidt or such as the polyglyceryl-4 isostearate/cetyl dimethicone copolyol/hexyl laurate mixture sold under the name Abil WE 09 by the company Goldschmidt, oleyl dimethicone copolyol, such as that sold under the name KF-6026 by the Company Shin-Etsu, or stearyl dimethicone copolyol, such as that sold under the name X-22-904 by the Company Shin-Etsu.

In the expression "crosslinked elastomeric solid organopolysiloxanes comprising at least one oxyalkylenated group," the term "elastomeric" is understood to mean a flexible and deformable material having viscoelastic properties and in particular the consistency of a sponge or of a flexible sphere. Its modulus of elasticity is such that this material is resistant to deformation and has a limited ability to expand and to contract. This material is capable of returning to its original shape after it has been stretched. This elastomer is formed of polymeric chains of high molecular weight, the mobility of which is limited by a uniform network of crosslinking points.

The crosslinked elastomeric solid organopolysiloxanes useful in the composition of the invention comprise one or more oxyalkylenated groups and preferably oxyethylenated (OE) groups, for example from 1 to 40 oxyalkylene units and better still 1 to 20 oxyalkylene units, which can form polyoxyalkylene chains and in particular polyoxyethylene chains. These groups can be pendant, at the chain end or intended to bond two parts of the silicone structure. The silicon atoms carrying these groups preferably number from approximately 1 to 10.

Although the invention relates preferably to crosslinked elastomeric solid organopolysiloxanes with (an) oxyethylenated group(s), it includes organopolysiloxanes with (an) oxypropylenated group(s). The organopolysiloxanes can also comprise both one or more oxyethylenated (OE) group (s), for example 1 to 20, and one or more oxypropylenated (OP) group(s), for example 0 to 20; these organopolysiloxanes are also known as organopolysiloxanes with (an) alkylethoxy-propylenated group(s). The number of oxyethylenated groups is preferably greater than the number of oxypropylenated groups.

The crosslinked elastomeric solid organopolysiloxanes which can be used in the composition of the invention are partially or completely crosslinked and have a three-dimensional structure. When included in an oily phase, they are converted, according to the level of oily phase used, from a product with a spongy appearance, when they are used in the presence of low contents of oily phase, into a homogeneous gel, in the presence of larger amounts of oily phase. The gelling of the oily phase by these elastomers can be complete or partial.

These organopolysiloxanes can be provided in the form of a powder, the particles constituting this powder having a size ranging from 0.1 to 500 μm and better still from 3 to 200 μm and being able to be spherical, flat or amorphous with preferably a spherical shape. They can also be provided in the form of a gel comprising the elastomeric organopolysiloxane dispersed in an oily phase. This oily phase, also known as liquid fatty phase, can comprise any non-aqueous substance or mixture of non-aqueous substances which is liquid at room temperature (25° C.).

These elastomeric organopolysiloxanes include the crosslinked polymers obtained by an addition and crosslinking reaction in a non-aqueous medium, in the presence of a catalyst of the platinum type, of at least:

(a) one first organopolysiloxane (i) having at least two vinyl groups in the α,ω-position of the silicone chain; and (b) one second organopolysiloxane (ii) having at least one hydrogen atom bonded to a silicon atom per molecule and at least one oxyalkylenated, preferably oxyethylenated, group.

Preferably, the organopolysiloxane (i) is chosen from polydimethylsiloxanes (PDMSs) and is more especially an α,ω-dimethylvinylpolydimethylsiloxane. The organopolysiloxane (ii) is preferably chosen from polydimethylsiloxanes comprising one or more hydrogen atom(s), each bonded to a silicon atom, and one or more oxyethylenated groups and optionally one or more oxypropylenated groups, which groups are bonded to a silicon atom via an alkylene radical having from 1 to 22 carbon atoms.

The silicone chains of the first and second organopolysiloxanes (i) and (ii) optionally comprise $C_1$ to $C_6$ alkyl pendant chains and/or aryl chains.

As indicated hereinabove, the elastomeric organopolysiloxanes useful in the composition according to the invention are advantageously provided in an oily phase, with which they constitute an anhydrous gel. This gel can be obtained in particular as follows:

(a) mixing the first organopolysiloxane (i) and the second organopolysiloxane (ii);

(b) adding an oily phase to the mixture of the stage (a); and (c) polymerizing the first organopolysiloxane (i) and the second organopolysiloxane (ii) in the oily phase in the presence of a platinum catalyst.

The oily phase used during the manufacture of the anhydrous gel preferably comprises one or more oils which are liquid at room temperature (25° C.) chosen from hydrocarbonaceous oils and/or silicone oils. The oily phase is advantageously a silicone liquid phase comprising one or more oils chosen from PDMSs with a linear or cyclic chain which are liquid at room temperature, optionally comprising a pendant alkyl or aryl chain or an alkyl or aryl chain at the chain end, the alkyl chain having from 1 to 6 carbon atoms.

The organopolysiloxanes of the invention may be obtained according to the procedure of Examples 3, 4 and 8 of U.S. Pat. No. 5,412,004 and of the examples of U.S. Pat. No. 5,81 1,487, both incorporated herein in their entirety.

Elastomeric organopolysiloxanes which can be used in the composition of the invention include for example, that sold under the reference KSG 21 by the company Shin Etsu or the product of Example 3 (synthetic example) of Patent U.S. Pat. No. 5,412,004. KSG 21 is provided in the form of a gel and comprises 28% of organopolysiloxane and 72% of silicone oil (PDMS) having a viscosity of 6 cSt.

The product of Example 3 (synthetic example) of U.S. Pat. No. 5,412,004 is provided in the form of a pasty gel comprising approximately 32 to 33% by weight of crosslinked organopolysiloxane with (an) oxyethylenated group(s) and approximately 67 to 68% of PDMS 6 cSt. The organopolysiloxane comprises approximately 18% of ethylene oxide by weight with respect to the total weight of the polymer. This elastomeric gel has a plastic shear thinning behaviour of $2 \times 10^6$ poises to $4 \times 10^6$ poises and a dynamic viscosity of 45 poises for a shear rate of 200 $s^{-1}$, measured with an RS 75 (Haake) controlled-stress rheometer at 25° C. in cone/plate geometry; characteristics of the cone: diameter of 20 mm, angle of 1° and gap of 40 μm. This organopolysiloxane additionally has a viscoelastic behaviour with a dominant elastic nature at low values of the shear stress defined as follows: 800 Pa<$G^+_{plate}$<2500 Pa with $\delta_{plate}$ in the region of 10°, $G^+_{plate}$ representing the consistency and $\delta_{plate}$ representing the elasticity. It exhibits a flash point of approximately 170° C. at atmospheric pressure.

The silicone emulsifier present in the composition of the invention preferably is present in an amount of from 0.1 to 10%, better still from 0.3 to 5% and even better still from 0.4 to 2.5% by weight with respect to the total weight of the composition, including 0.5, 1, 2, 3, 4, 5, 6, 7, 8 and 9% of all ranges and values thereinbetween.

The oily phase/silicone emulsifier ratio by weight is preferably equal to or greater than 5 and better still equal to or greater than 8.

The invention composition comprises at least one wax. Mixtures may be used. Included are waxes of animal origin, such as beeswax, spermaceti, lanolin wax and lanolin derivatives; waxes of vegetable origin, such as carnauba, candelilla, ouricury, or japan wax, cocoa butter, or cork fibre or sugarcane waxes; mineral waxes, for example paraffin wax, petrolatum wax, lignite wax, microcrystalline waxes or ozokerites; synthetic waxes, including polyethylene or polytetrafluoroethylene waxes and waxes obtained by the Fischer-Tropsch synthesis; silicone waxes; or hydrogenated oils which are solid at 25° C., such as hydrogenated castor oil, hydrogenated jojoba oil, hydrogenated palm oil, hydrogenated tallow, hydrogenated coconut oil and fatty esters which are solid at 25° C., such as the $C_{20}$–$C_{40}$ alcyl stearate sold under the trade name "Kester Wax K82H" by the company Koster Keunen.

Useful silicone waxes include for example, polyether silicone waxes or alkyl or alkoxy dimethicones having from 16 to 45 carbon atoms, such as the poly (methylalkyldimethylsiloxane) sold under the name DC 2493 by the company Dow Corning (CTFA name: C30–45 alkyl methicone).

According to a preferred embodiment of the invention, the composition comprises, as wax, polyethylene wax or better still a mixture of polyethylene wax and hydrogenated jojoba oil.

The composition of the invention comprises an amount of wax(es) of at least 3% and preferably ranging from 3 to 10% and better still from 5 to 8% by weight with respect to the total weight of the composition including 4, 5, 6, 7, 8, and 9% and all ranges and values thereinbetween.

The oily phase of the composition according to the invention can include, in addition to the wax and the oil which is optionally present as a mixture with the silicone emulsifier, any kind of oil and of fatty substance known to a person skilled in the art, for example oils of vegetable origin jojoba, avocado, sesame, sunflower, maize, soybean, safflower or grape seed oils), mineral oils (optionally hydrogenated isoparaffins or liquid paraffin), synthetic oils (purcellin oil, mixture of isopropyl myristate and cetearyl octanoate; polyisobutylene; ethylhexyl palmitate; or alkyl benzoates), volatile or non-volatile silicone oils, such as polydimethylsiloxanes (PDMSs) and cyclodimethylsiloxanes or cyclomethicones, and fluorinated or fluorosilicone oils, as well as the mixtures of these oils.

The oily phase can, in addition, comprise other fatty constituents, such as fatty alcohols, for example stearyl alcohol, cetyl alcohol and cetearyl alcohol, and fatty acids.

The oily phase is present in the composition according to the invention in an amount ranging from 7 to 25% and preferably from 10 to 20% by weight with respect to the total weight of the composition including 11, 13, 15, 17 and 19% and all values and ranges thereinbetween.

Another advantage of the composition according to the invention results from the fact that it is possible to incorporate a large amount of at least one electrolyte or of a mixture of electrolytes in the composition without having a detrimental effect on the stability of the composition.

Useful electrolytes include for example, the salts of mono-, di- or trivalent metals and more particularly alkaline earth metal salts, such as barium, calcium and strontium salts; alkali metal salts, such as sodium and potassium salts, magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminium, silicon and selenium salts, and their mixtures.

The ions constituting these salts can be chosen, for example, from carbonates, bicarbonates, sulphates, glycerophosphates, borates, chlorides, bromides, nitrates, acetates, hydroxides or persulphates, as well as salts of α-hydroxy acids (citrates, tartrates, lactates or malates) or fruit acids, or alternatively salts of amino acids (aspartate, arginate, glycocholate or fumarate).

The electrolyte is preferably a mixture of salts comprising in particular calcium, magnesium and sodium salts and in particular a mixture comprising at least magnesium chloride, potassium chloride, sodium chloride, calcium chloride and magnesium bromide, the said mixture corresponding to Dead Sea salts.

The content of electrolyte(s), when the composition comprises it/them, generally ranges from 0.5 to 20% and preferably from 2 to 10% by weight with respect to the total weight of the composition.

The composition according to the invention preferably is, or is contained within, a physiologically acceptable medium and may constitute in particular a cosmetic or dermatological composition. It has applications in a large number of treatments, in particular cosmetic treatments, of the skin, including the scalp, hair, nails and/or mucous membranes, in particular for caring for, cleansing, making up and/or the antisun protection of the skin and/or mucous membranes, as well as for the preparation of a cream intended for the treatment of the skin, more particularly of greasy skin (contribution of freshness).

Thus, one embodiment of the present invention is the cosmetic use of the composition as defined hereinabove for treating, protecting, caring for, removing make-up from and/or cleansing the skin, lips and/or hair and/or for making up the skin and/or lips.

Another embodiment of the present invention is a process for the treatment (cosmetic, dermatological, etc.) of the skin, including the scalp, hair and/or lips, characterized in that a composition as defined hereinabove is applied to the skin, hair and/or lips.

Another embodiment of the invention is the use of the composition as defined hereinabove in the manufacture of a cream intended for the treatment of greasy skin.

The composition of the invention may also comprise adjuvants usual in the cosmetics and/or dermatological fields, such as active principles, preservatives, antioxidants, complexing agents, solvents, fragrances, fillers, bactericides, odour absorbers, colouring materials and lipid vesicles. The amounts of these various adjuvants are those conventionally used in the field under consideration, for example from 0.01 to 20% of the total weight of the composition. These adjuvants, depending on their nature, can be introduced into the fatty phase, into the aqueous phase and/or into the lipid vesicles.

Mention may in particular be made, as active principles, of, in addition to the electrolytes indicated hereinabove, sunscreens, moisturizing agents, for example protein hydrolysates, polyols, such as glycerol, glycols, such as polyethylene glycols, and sugar derivatives; natural extracts; procyanidol oligomers; vitamins; urea; depigmenting agents, such as kojic acid and caffeic acid; β-hydroxy acids, such as salicylic acid and its derivatives; α-hydroxy acids, such as lactic acid and glycolic acid; retinoids, such as carotenoids; or screening agents, and their mixtures.

The active principle or principles can be present, for example, in a concentration ranging from 0.01 to 20%, preferably form 0.1 to 5% and better still from 0.5 to 3% of the total weight of the composition.

The composition according to the invention can be prepared, for example, by introducing the aqueous phase into the oily phase and by casting the mixture under warm conditions, or else by cooling the mixture while maintaining very slow mixing until the temperature has returned to room temperature (20–25° C.). The composition has a solid or else "grainy" appearance, that is to say that it has a novel granular appearance which gives variety to the range of textures having a fresh effect.

The examples hereinbelow of compositions according to the invention are given by way of illustration and without limiting the invention. The amounts are given as % by weight, unless otherwise mentioned.

EXAMPLE 1

Refreshing Solid Cream

| Phase A: | |
| --- | --- |
| Purcellin oil (cetearyl octanoate/ isopropyl myristate) | 2.44% |
| Hydrogenated jojoba oil | 5.5% |
| Polyethylene wax | 0.8% |
| Example 3 of US-5,412,004, comprising 32% of organopolysiloxane (i.e., 1.54% of organopolysiloxane) | 4.82% |
| Phase B: | |
| Hexacyclomethicone | 4.44% |
| Purcellin oil (cetearyl octanoate/ isopropyl myristate) | 2% |
| Phase C: | |
| Glycerol | 2% |
| Sodium chloride | 0.5% |
| Water | q.s. for 100% |

Procedure: Phase C is placed on a water bath at 90° C. Phase A is furthermore melted at approximately 80–85° C. on a heating plate while being stirred with a spatula and is then placed on a water bath. Phase B is rapidly added to phase A, which is maintained on the water bath, and phase C is poured into the mixture obtained with stirring. The emulsion obtained is cast into dishes and is then left to cool to room temperature, preferably while covering the dish.

A solid cast cream is obtained which gives beads on being taken up, that is to say that water forms beads on the product when the product is taken up with the finger from the dish.

EXAMPLE 2

Cast Cream

| Phase A: | |
| --- | --- |
| Purcellin oil (cetearyl octanoate/ isopropyl myristate) | 2.64% |
| Hydrogenated jojoba oil | 5.5% |
| Polyethylene wax | 0.8% |
| Abil WE09 | 1.92% |
| Phase B: | |
| Hexacyclomethicone | 4.59% |

| -continued | |
| --- | --- |
| Purcellin oil (cetearyl octanoate/ isopropyl myristate) | 2% |
| Phase C: | |
| Glycerol | 2% |
| Sodium chloride | 0.5% |
| Water | q.s. for 100% |

Procedure: Identical to that of Example 1.

A cast cream is obtained which is very fresh on application.

French application 9909013 is incorporated herein by reference.

What is claimed is:

1. A solid composition comprising
   an aqueous phase, and
   an oily phase, which includes
      a silicone emulsifier and
      a wax, wherein
   the aqueous phase is dispersed in the oily phase;
   the aqueous phase is present in at least 75% by weight with respect to the total weight of the composition;
   the wax is present in at least 3% by weight with respect to the total weight of the composition;
   the solid composition exhibits a compressive strength of greater than or equal to 50 grams, at room temperature, after penetration by a cylindrical probe having a diameter of 0.8 cm into the composition over a thickness of 5 mm at a rate of 1 mm/s;
   the oily phase/silicone emulsifier ratio by weight is equal to or greater than 5; and
   the composition comprises at least 70% water with respect to the total weight of the composition.

2. The composition according to claim 1, wherein the silicone emulsifier is selected from the group consisting of dimethicone copolyols, alkyl or alkoxy dimethicone copolyols, crosslinked elastomeric solid organopolysiloxanes comprising at least one oxyalkylenated group, and mixtures thereof.

3. The composition according to claim 1, wherein the silicone emulsifier is selected from the group consisting of lauryl dimethicone copolyol, cetyl dimethicone copolyol, oleyl dimethicone copolyol, stearyl dimethicone copolyol, and mixtures thereof.

4. The composition according to claim 1, wherein said silicone emulsifier is a crosslinked elastomeric solid organopolysiloxane comprising at least one oxyethylene group.

5. The composition according to claim 2, wherein the silicone emulsifier is a crosslinked elastomeric solid organopolysiloxane, said organopolysiloxane obtained by an addition and crosslinking reaction in a non-aqueous medium, in the presence of a catalyst, of at least:
   one first organopolysiloxane (i) having two vinyl groups in the, -position of the silicone chain per molecule; and
   one second organopolysiloxane (ii) having at least one hydrogen atom bonded to a silicon atom per molecule and at least one oxyalkylenated group.

6. The composition according to claim 5, wherein the first organopolysiloxane (i) is a polydimethylsiloxane.

7. The composition according to claim 5, wherein the first organopolysiloxane (i) is an α,ω-dimethylvinylpolydimethylsiloxane.

8. The composition according to claim 5, wherein the second polyorganosiloxane (ii) is chosen from polydimethylsiloxanes having one or more hydrogen atoms and one or more oxyalkylenated groups bonded to a silicon atom via an alkylene radical having from 1 to 22 carbon atoms.

9. The composition according to claim 1, wherein the silicone emulsifier is an organopolysiloxane that is in the form of a gel obtained according to the following stages:

(a) mixing first and second organopolysiloxanes (i) and (ii);

(b) adding an oily phase to the mixture of the stage (a);

(c) polymerizing the first and second organopolysiloxanes (i) and (ii) in the oily phase in the presence of a platinum catalyst.

10. The composition according to claim 1, wherein the silicone emulsifier is present in an amount of 0.1 to 10% by weight with respect to the total weight of the composition.

11. The composition according to claim 1, wherein the wax is selected from the group consisting of waxes of animal origin, waxes of vegetable origin, mineral waxes, synthetic waxes, silicone waxes, hydrogenated oils which are solid at 25° C., fatty esters which are solid at 25° C., and mixtures thereof.

12. The composition according to claim 1, wherein the amount of wax in the composition ranges from 3 to 10% by weight with respect to the total weight of the composition.

13. The composition according to claim 1, wherein the oily phase is present in an amount ranging from 7 to 25% by weight with respect to the total weight of the composition.

14. The composition according to claim 1, wherein the oily phase/silicone emulsifier ratio by weight is equal to or greater than 8.

15. The composition according to claim 1, further comprising at least one electrolyte.

16. The composition according to claim 15, wherein said electrolyte is present in an amount ranging from 0.5 to 20% of the total weight of the composition.

17. The composition according to claim 1, further comprising an active principle selected from the group consisting of sunscreens, moisturizing agents, natural extracts, procyanidol oligomers, vitamins, urea, depigmenting agents, β-hydroxy acids, α-hydroxy acids, retinoids, screening agents and mixtures thereof.

18. The composition according to claim 1, wherein said composition is a cosmetic composition.

19. A method for treating, protecting, caring for, removing make-up from and/or cleansing the skin, lips and/or hair and/or for making up the skin and/or lips, comprising applying the composition of claim 1 to the hair, skin and/or lips.

20. A method for treating greasy skin, comprising applying the composition of claim 1 to greasy skin, wherein said composition is in the form of a cast cream.

21. A method of making a composition, the method comprising dispersing an aqueous phase in an oily phase; and forming the composition of claim 1.

22. A method of using a composition, the method comprising preparing a cream from the solid composition of claim 1; and applying the cream to skin.

23. The composition according to claim 1, wherein the wax is present in at least 5% by weight with respect to the total weight of the composition.

24. The composition according to claim 1, wherein the wax is present in 5% to 8% by weight with respect to the total weight of the composition.

25. The composition according to claim 1, wherein the aqueous phase is present in an amount ranging from 75% to 92% by weight with respect to the total weight of the composition.

26. The composition according to claim 12, wherein the aqueous phase is present in an amount ranging from 75% to 92% by weight with respect to the total weight of the composition.

27. The composition according to claim 1, wherein the oily phase comprises oils selected from the group consisting of silicone oils and hydrocarbon oils.

28. The composition according to claim 27, wherein the oils consist of hydrocarbon oils.

29. The composition according to claim 27, wherein the oils consist of silicone oils.

* * * * *